(12) United States Patent
Maroney et al.

(10) Patent No.: US 6,702,824 B2
(45) Date of Patent: *Mar. 9, 2004

(54) PROSTHESIS POSITIONING APPARATUS

(75) Inventors: Brian J. Maroney, Fort Wayne, IN (US); Charles A. Rockwood, Jr., San Antonio, TX (US); Reese K. Myers, Warsaw, IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 263 days.

This patent is subject to a terminal disclaimer.

(21) Appl. No.: 09/892,688

(22) Filed: Jun. 27, 2001

(65) Prior Publication Data

US 2001/0037115 A1 Nov. 1, 2001

Related U.S. Application Data

(63) Continuation of application No. 09/394,557, filed on Sep. 10, 1999, now Pat. No. 6,277,123.

(51) Int. Cl.[7] ............................................... A61B 17/90
(52) U.S. Cl. ....................................................... 606/99
(58) Field of Search ............................. 606/53, 54, 86, 606/87, 88, 89, 99, 102; 623/19.11–19.14, 22.12

(56) References Cited

U.S. PATENT DOCUMENTS

| 3,814,089 A | 6/1974 | Deyerle |
| 3,945,377 A | 3/1976 | Kronner |
| 4,357,716 A | 11/1982 | Brown |
| 4,624,250 A | 11/1986 | Saunders et al. |
| 4,718,414 A | 1/1988 | Saunders et al. |
| 4,893,619 A | 1/1990 | Dale et al. |
| 4,959,066 A | 9/1990 | Dunn et al. |
| 4,968,316 A | 11/1990 | Hergenroeder |
| 5,047,061 A | 9/1991 | Brown |
| 5,108,396 A | 4/1992 | Lackey et al. |

(List continued on next page.)

FOREIGN PATENT DOCUMENTS

| DE | 298 05 703 U | 8/1998 |
| FR | 2 770 128 A | 4/1999 |
| GB | 747 876 A | 4/1956 |
| WO | WO 97 27828 | 8/1997 |

OTHER PUBLICATIONS

TORNIER Shoulder Prosthesis Aequalis fracture jig brochure.

Cofield[2] Total Shoulder System: Surgical Technique catalog by Robert H. Cofield, M.D., Smith + Nephew, Inc., Memphis, Tennessee, 31 pages.

Primary Examiner—David O. Reip
(74) Attorney, Agent, or Firm—Maginot, Moore & Beck

(57) ABSTRACT

An apparatus for positioning a prosthesis in a bone includes a body, first and second clamps, a depth gauge and a guide. The first clamp is coupled to the body. The depth gage is coupled to the body and is movable relative thereto generally perpendicular to the shaft of the bone. The second clamp can be selectively engaged with and disengaged from the depth gage. The second clamp is movable with the depth gage and is also moveable in a direction generally parallel to the axis of the bone. The guide is used to determine the proper rotational orientation of the apparatus. The first clamp is then secured to the bone. The second clamp is secured to a trial prosthesis and is engaged with the depth gage as the trial is inserted into the bone. When the proper insertion depth is reached, the second clamp is secured to the depth gage. The joint is then reduced and the range of motion checked. The depth and rotational orientation may be adjusted as needed. The second clamp is released from the trial, the trial is removed and the prosthesis is inserted in the bone and secured to the second clamp.

23 Claims, 5 Drawing Sheets

U.S. PATENT DOCUMENTS

| | | |
|---|---|---|
| 5,171,324 A | 12/1992 | Campana et al. |
| 5,207,682 A | 5/1993 | Cripe |
| 5,228,459 A | 7/1993 | Caspari et al. |
| 5,312,409 A | 5/1994 | McLaughlin et al. |
| 5,364,401 A | 11/1994 | Ferrante et al. |
| 5,374,271 A | 12/1994 | Hwang |
| 5,409,489 A | 4/1995 | Sioufi |
| 5,429,641 A | 7/1995 | Gotfried |
| 5,431,656 A | 7/1995 | Clift, Jr. et al. |
| 5,437,676 A | 8/1995 | Bouraly et al. |
| 5,476,466 A | 12/1995 | Barrette et al. |
| 5,514,143 A | 5/1996 | Bonutti et al. |
| 5,520,694 A | 5/1996 | Dance et al. |
| 5,578,039 A | 11/1996 | Vendrely et al. |
| 5,601,566 A | 2/1997 | Dance et al. |
| 5,607,431 A | 3/1997 | Dudasik et al. |
| 5,611,802 A | 3/1997 | Samuelson et al. |
| 5,624,443 A | 4/1997 | Burke |
| 5,628,749 A | 5/1997 | Vendrely et al. |
| 5,628,750 A | 5/1997 | Whitlock et al. |
| 5,645,548 A | 7/1997 | Augsburger |
| 5,704,941 A | 1/1998 | Jacober et al. |
| 5,779,709 A | 7/1998 | Harris, Jr. et al. |
| 5,951,561 A | 9/1999 | Pepper et al. |
| 5,951,564 A | 9/1999 | Schroder et al. |
| 5,961,555 A | 10/1999 | Huebner |
| 5,976,149 A | 11/1999 | Masini |
| 5,997,543 A | 12/1999 | Truscott |
| 6,102,953 A | 8/2000 | Huebner |
| 6,168,627 B1 | 1/2001 | Huebner |
| 6,168,628 B1 | 1/2001 | Huebner |
| 6,193,758 B1 | 2/2001 | Huebner |
| 6,267,785 B1 | 7/2001 | Masini |
| 6,277,123 B1 | 8/2001 | Maroney et al. |

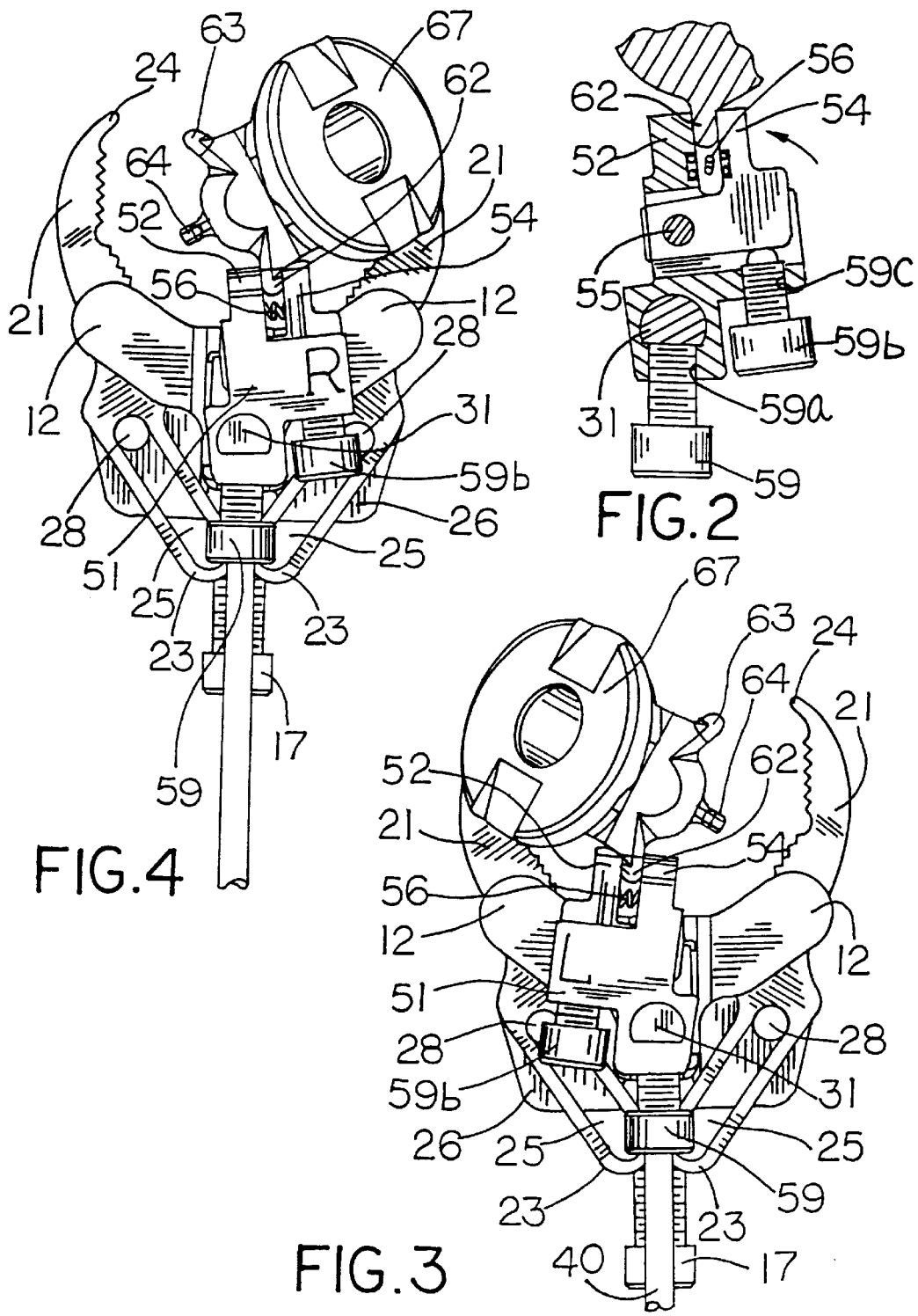

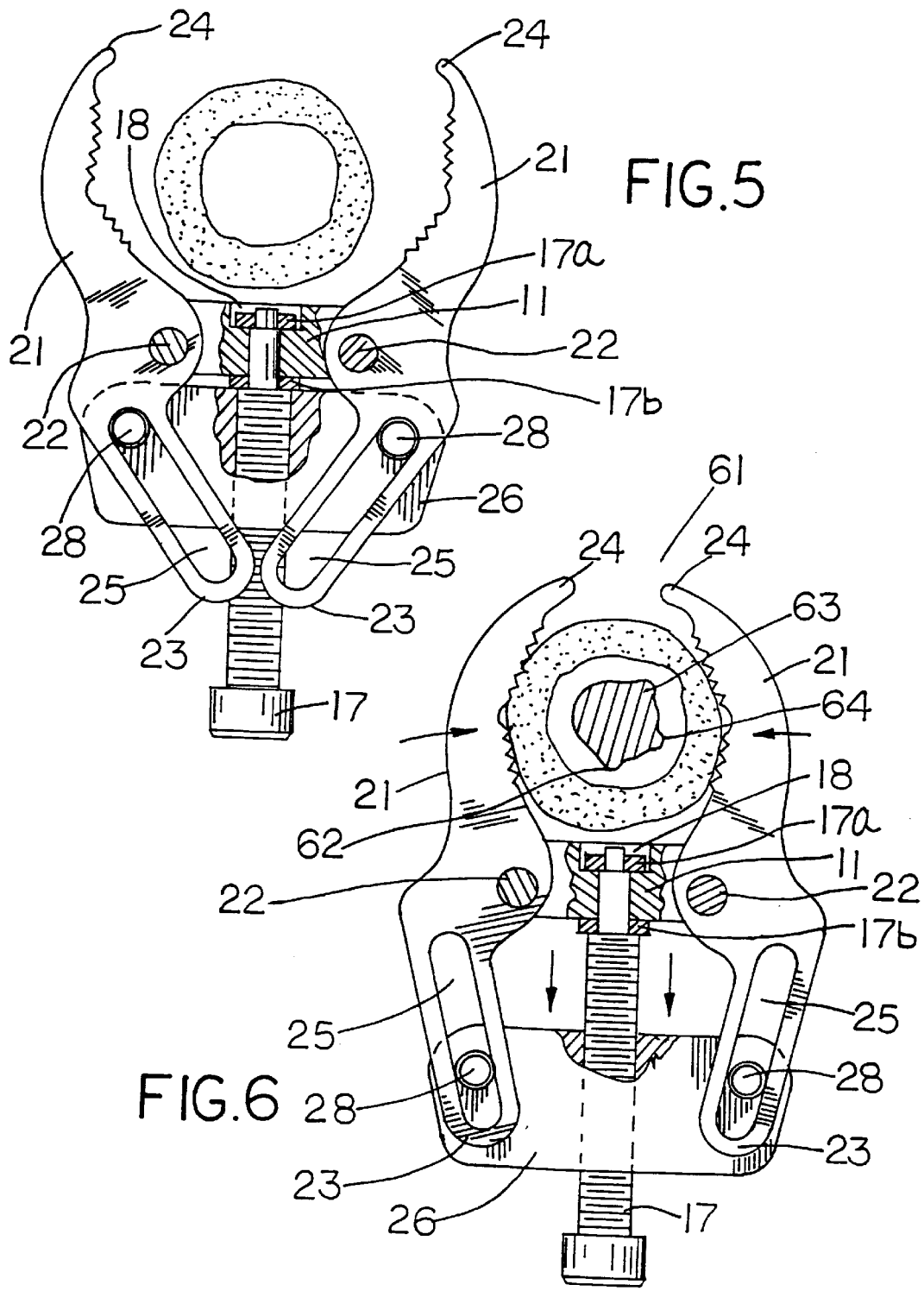

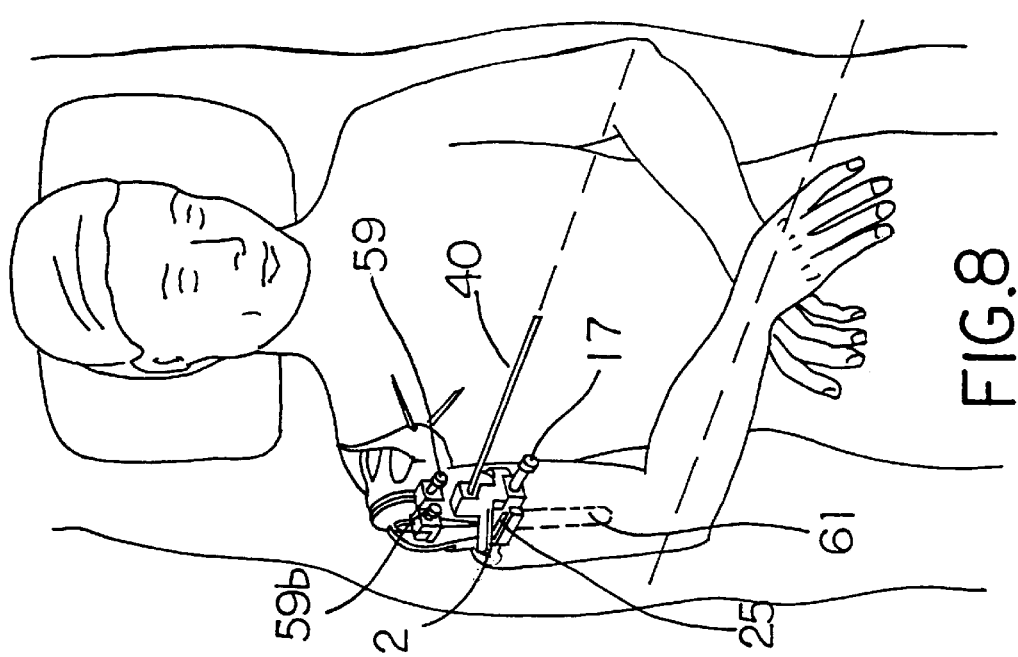
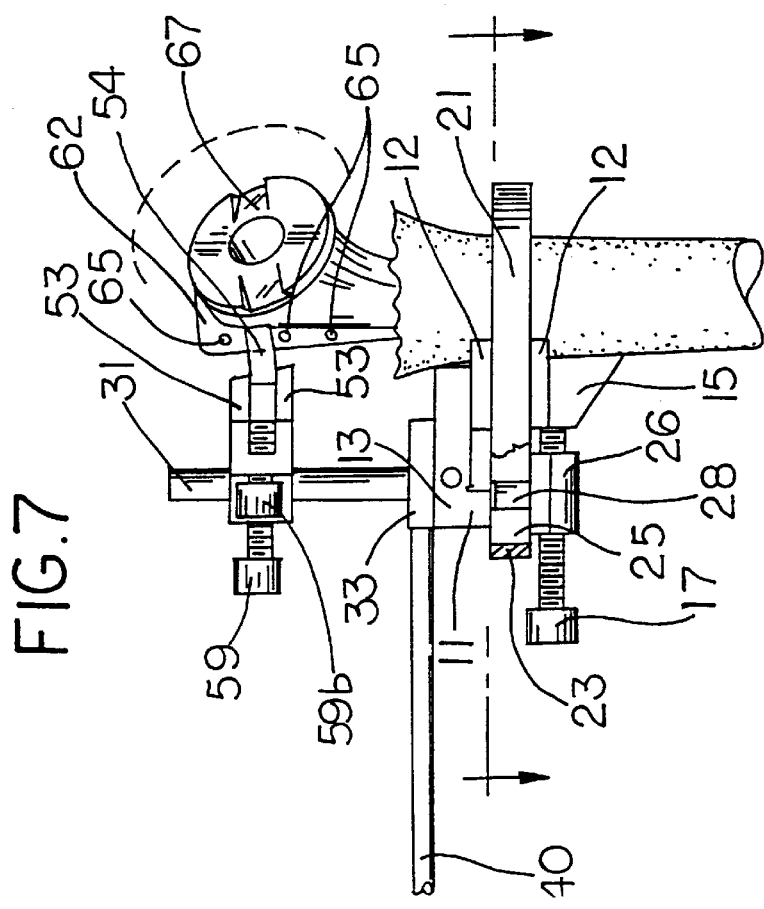

PROSTHESIS POSITIONING APPARATUS

This application is a continuation of co-pending application Ser. No. 09/394,557, filed on Sep. 10, 1999, now U.S. Pat. No. 6,277,123.

BACKGROUND AND SUMMARY OF THE INVENTION

The present invention relates to a device for positioning a prosthesis in a bone and a method of implanting a prosthesis.

Various prostheses are known for replacing all or part of a damaged or diseased joint. For example, prostheses for replacing all or a portion of a damaged or diseased knee, hip and shoulder of a person are well known. Often, the joint is replaced by securing one portion of the prosthesis to one bone of the joint and another portion of the prosthesis to another bone.

When reconstructing damaged or diseased joints with artificial prostheses, it is desirable to position the components of the prosthesis such that the structure and function of a properly functioning natural joint is replicated to the greatest degree possible. This involves consideration of several factors. For example, the components of the prosthesis must be inserted such that the patient has the desired limb length after the surgery. It is also desirable that the range of motion of the joint postoperative is, to the extent possible, the same as that of a healthy joint. Some of the factors relevant to proper placement include insertion depth of the prosthesis components into the bone and rotational orientation of the prosthesis components.

The present invention provides an apparatus for positioning a prosthesis in a bone. According to one embodiment of the invention, an apparatus for positioning a prosthesis having a stem in the intermedullary canal of a bone includes a body, a first clamp connected to the body for engaging the bone, a depth gage connected to the body for determining the depth of the prosthesis stem within the intermedullary canal, and a second clamp connected to the depth gage for engaging the prosthesis. The body may include a projection for stabilizing the apparatus when the first clamp engages the bone. A plurality of markings may be provided on the depth gage. The apparatus may include a guide for determining proper rotational orientation of the apparatus relative to the bone. The guide may be selectively secured to and removed from the body. The second clamp may be movable relative to the first clamp. The depth gage may be movable with respect to the first clamp and/or the body. The second clamp may be movable relative to the depth gage. The body may be provided with a channel and the depth gage may be connected to a base that is movable within the channel. The base may include a slot and the channel may include a stop for limiting movement of the base in the channel. The second clamp may be removable from the depth gage and may be engaged with the depth gage in at least two orientations. A cam may be provided for adjusting the first clamp. In one embodiment, the first clamp includes a pair of jaws that engage the shaft of the bone after the soft tissue is removed.

In another embodiment of the present invention, an apparatus for positioning a prosthesis having a stem in the intermedullary canal of a bone having a shaft includes a body, a first clamp for engaging the bone, the first clamp being coupled to the body, a depth gage for determining the depth of insertion of the prosthesis stem in the intermedullary canal, the depth gage being coupled to the body and moveable relative to the body in a direction generally perpendicular to the shaft of the bone, and a second clamp for engaging the prosthesis, the second clamp being coupled to the depth gage for movement therewith and being movable relative to the body in a first direction generally parallel to the shaft of the bone.

According to another embodiment of the present invention, an apparatus for positioning a prosthesis having a stem in the intermedullary canal of a bone includes first means for selectively attaching the apparatus to the bone, second means for determining the depth of insertion of the prosthesis stem in the intermedullary canal, the second means being coupled to the first means, third means for selectively engaging the prosthesis, the third means being coupled to the second means, fourth means for permitting movement of the third means relative to the first means in a first direction, and fifth means for permitting movement of the third means relative to the first means in a second direction. The first means may include a clamp and a cam for operating the clamp. The second means may include a post, which may include at least one marking. The third means may include a clamp. The fourth means may include a post and an opening in the third means that engages the post. The fifth means may include a body moveable within a channel and the third means may be coupled to the body. The apparatus may also include a stop in the channel for limiting movement of the body.

According to another embodiment of the invention, a method of implanting a prosthesis having a stem in the intermedullary canal of a bone includes the steps of reaming the intermedullary canal to accommodate at least a portion of the stem, providing an apparatus having a first clamp, a second clamp, a depth gage and a guide, using the guide to establish the proper rotational orientation of the apparatus, securing the first clamp to the bone, securing the second clamp to the prosthesis, coupling the second clamp to the depth gage, inserting the stem into the intermedullary canal, and reducing the joint.

Other features of the present invention will be apparent to those skilled in the art from the detailed description of the preferred embodiments and the accompanying drawings.

BRIEF DESCRIPTION OF THE DRAWINGS

FIG. 2 is a partial cross-sectional view showing a clamp that forms a component of the apparatus of FIG. 1 secured to a humeral prosthesis.

FIG. 3 is a top plan view showing the apparatus of FIG. 1 secured to a prosthesis for use in a left humerus.

FIG. 4 is a top plan view showing the apparatus of FIG. 1 secured to a prosthesis for use in a right humerus.

FIG. 5 is a partial cross-sectional, top plan view showing the apparatus of FIG. 1 positioned about a humerus prior to engagement with the humerus.

FIG. 6 is a partial cross-sectional, top plan view showing the apparatus of FIG. 1 engaging a humerus with the prosthesis planted within the intermedullary canal of the bone.

FIG. 7 is a side plan view showing the apparatus of FIG. 1 secured to a humeral prosthesis and a humerus.

FIG. 8 shows the apparatus of FIG. 1 in use.

DETAILED DESCRIPTION OF THE PREFERRED EMBODIMENTS

Figure 1:
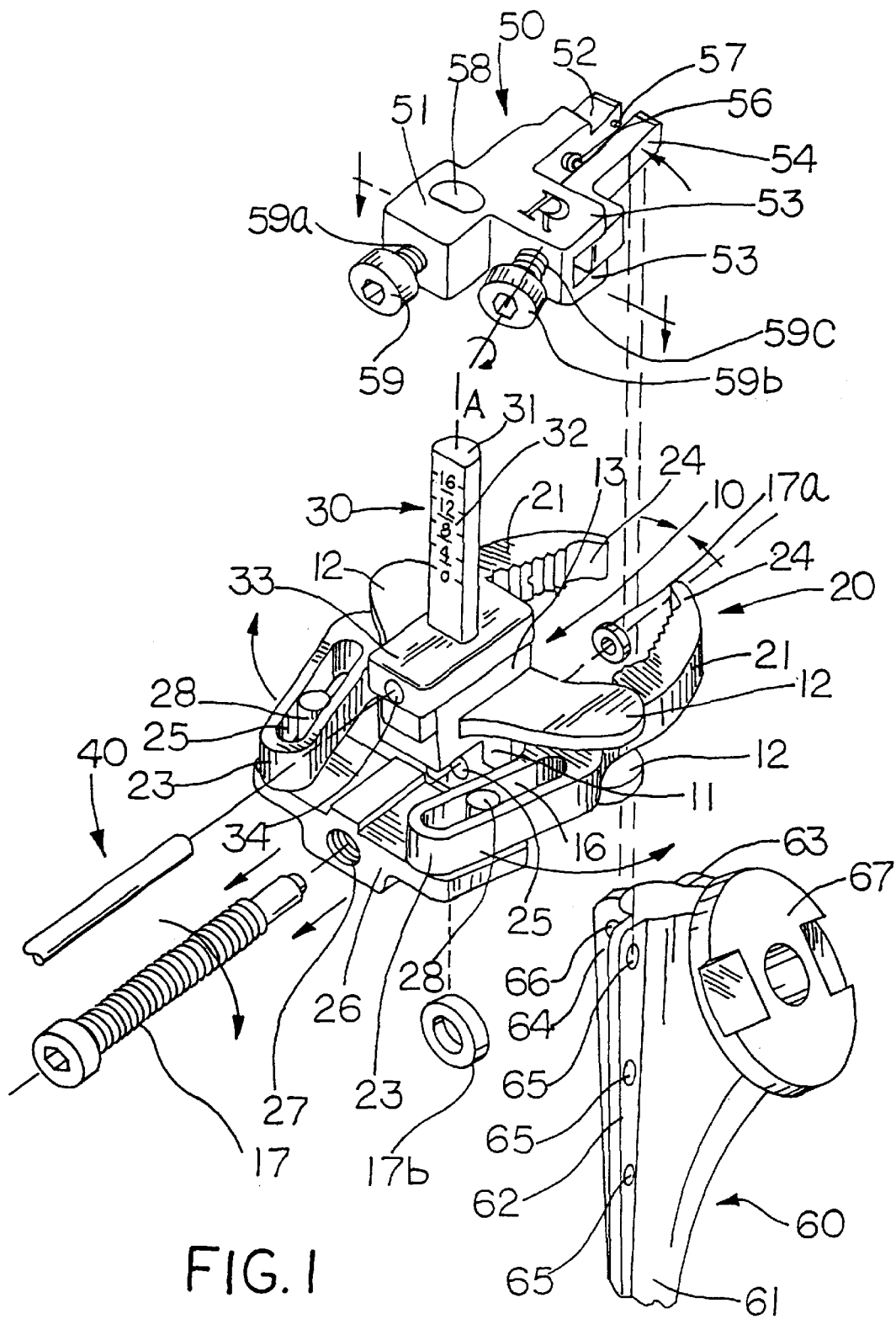
FIG. 1 is an exploded perspective view of an apparatus for positioning a prosthesis in a bone according to one embodiment of the present invention and a humeral prosthesis.
Figure 1A:
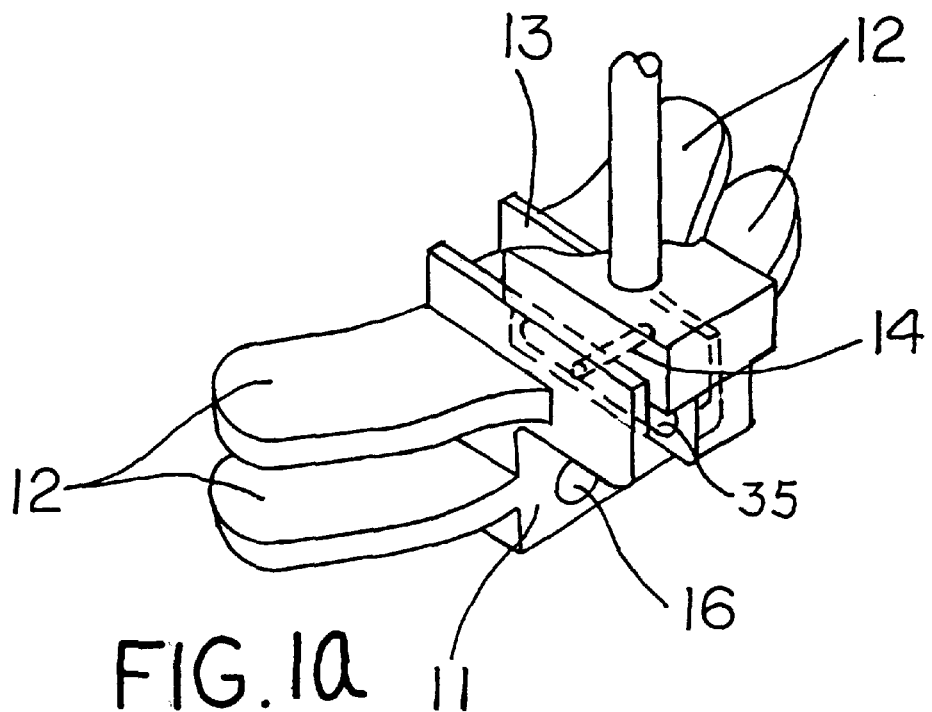
FIG. 1a is a perspective view of a body and depth gage that are components of the apparatus of FIG. 1.

FIG. 1 is an exploded perspective view of an apparatus for positioning a prosthesis in a bone according to one embodiment of the present invention. The apparatus generally includes a body 10, a first clamp 20, a depth gauge 30, a guide 40 and a second clamp 50. Body 10 generally includes a central portion 11 having a pair of spaced-apart arms 12 extending from each side thereof. Body 10 further includes a channel 13 having a stop 14 (FIG. 1a) in the form of a post extending across the width of channel 13. A projection 15 extends below channel 13. A bore 16 is formed in body 10 for receiving screw 17 as described below. A pair of washers 17a and 17b are provided for securing screw 17 to central portion 11 of body 10, as described below. Body 10 may be made from any of a number of materials suitable for use in the field of orthopaedic surgery.

First clamp 20 includes a pair of jaws 21 connected to arms 12 by pins 22. This is best shown in FIGS. 5 and 6, wherein the upper arms 12 and part of central portion 11 of body 10 have been removed to better illustrate bore 16, screw 17, washers 17a and 17b and pins 22. Each jaw 21 includes a first end 23 and a second end 24. In the embodiment shown, an opening or slot 25 is formed in each jaw 21 adjacent first end 23. Clamp 20 further includes a cam 26 having a threaded bore 27 therein. Bore 27 receives screw 17 to operate cam 26, as described below. A pair of pins 28 project from cam 26 and are located within openings 25 of jaws 21 as shown. As shown in FIGS. 5 and 6, washer 17a is located within a recessed area 18 of body 10. Washer 17b is located between central portion 11 of body 10 and cam 26. Both washers 17a and 17b are aligned with bores 16 and 27 such that screw 17 can pass through bores 16 and 27 and washers 17a and 17b.

Figure 1B:
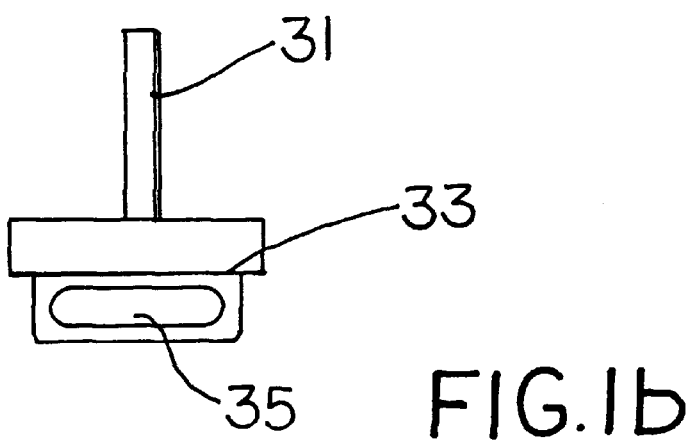
FIG. 1b is a side plan view of a depth gage that forms a component of the apparatus of FIG. 1.

Depth gauge 30, in the embodiment shown, includes a post 31 with a plurality of markings 32 thereon. In the embodiment shown, post 31 has a generally semicircular cross-section transverse to its longitudinal axis A. Post 31 is connected to a base 33 that rides within channel 13 of body 10, as described below. A first opening 34 is located in base 33 for receiving guide 40. A second opening 35 (FIGS. 1a and 1b) is located in base 33 and receives stop 14 located in channel 13 of body 10.

Guide 40, in the embodiment shown, is a rod configured to mate with opening 34 in base 33 of depth gauge 30. Guide 40 can be secured to and removed from base 33 as desired.

Second clamp 50 includes a body 51 having a first jaw 52 extending therefrom. Body 51 further includes a pair of spaced-apart arms 53 between which is located a second jaw 54. Jaw 54 is secured to body 51 by a pin 55 so as to be able to pivot with respect to body 51. This is best shown in FIG. 2, where one arm 53 and a portion of jaw 52 have been cutaway to show pin 55. A spring 56 is located between jaws 52 and 54. Spring 56 biases second jaw 54 into an open direction. Jaws 52 and 54 each include a projection 57 on the inner surface thereof. Body 51 further includes an opening 58 configured to engage post 31 of depth gauge 30, as described below. A first screw 59 extends into a threaded opening 59a in body 51 to secure second clamp 50 to depth gauge 30. A second screw 59b extends into a threaded opening 59c to move second jaw 54, as described below. Clamp 50 also includes indicia on body 51 in the form of the letters "R" and "L" to indicated the proper orientation of clamp 50, as described below.

Prosthesis 60 is shown in FIG. 1 as a humeral implant for replacing the proximal end of a human humerus. Prosthesis 60 includes a stem 61 with an anterior fin 62, a posterior fin 63 and a lateral fin 64 extending therefrom. In the embodiment shown, three suture holes 65 are formed in anterior fin 62 and posterior fin 63. A single suture hole 66 is formed in lateral fin 64. Prosthesis 60 further includes a connector 67 for receiving the head portion of the prosthesis.

In use, the humeral shaft is prepared by appropriately surfacing the resected portion of the shaft and reaming the intermedullary canal. The arm is then positioned such that the palm faces anteriorly and the ulna is at a substantially 90° angle to the humerus. Guide 40 is inserted in opening 34 and the apparatus is positioned such that guide 40 is substantially parallel to the ulna. First clamp 20 is then engaged with the shaft of the humerus. This is accomplished by rotating screw 17 with an appropriate tool so as to drive cam 26 in the posterior direction. This causes pins 28 to move within openings 25. As this occurs, pins 28 bear on the inner surfaces of openings 25. The spacing of pins 28 and the orientation of openings 25 is such that cam 26 causes ends 23 of arms 21 to move toward one another. This causes arms 21 to pivot about pins 22 and open at ends 24. Once the apparatus is properly positioned, screw 17 is rotated in the opposite direction to draw cam 26 in the anterior direction. This causes ends 23 of jaws 21 to move away from one another, thereby causing jaws 21 to pivot about pins 22 such that ends 24 approach each other. In this manner, clamp 20 is secured to the shaft of the humerus. Guide 40 may then be removed from opening 34.

Second clamp 50 is then secured to a trial prosthesis. This is accomplished by first orienting second clamp 50 such that the proper indicia, either L for left or R for right, is facing proximally. Screw 59b is then drawn outwardly so that spring 56 will bias jaw 54 away from jaw 52, thereby opening second clamp 50. Second clamp 50 is then positioned such that projections 57 are aligned with the center suture hole 65 on anterior fin 62. Screw 59b is then advanced so as to push arm 54 forward, thereby causing it to pivot about pin 55 and grasp anterior fin 62 such that projections 57 are located within suture hole 65.

The trial is then positioned above the previously reamed intermedullary canal such that stem 61 is aligned therewith and opening 58 in body 51 of second clamp 50 is positioned above post 31 of depth gauge 30 so as to be able to engage post 31. Shaft 61 is then inserted into the intermedullary canal and opening 58 is slid over post 31. When the desired insertion depth is reached, screw 59 is advanced so as to contact post 31 and secure second clamp 50 to depth gauge 30. Note that base 33 of depth gauge 30 can slide back and forth within channel 13 until stop 14 engages either end of opening 35. This allows anterior/posterior positioning of the prosthesis. Note that, in the embodiments shown, the configuration of opening 58 and post 31 are such that opening 58 may engage post 31 in two orientations depending on whether the prosthesis is to be implanted in a right arm or a left arm. Note also that, in the embodiments shown, the trial prosthesis will be oriented with 30° of retroversion if the preceding steps are followed. This is a result of the proper positioning of clamp 20, the orientation and configuration of post 31 and opening 58 and the positioning of anterior fin 62. In the embodiments shown, anterior fin 62 and posterior fin 63 are both positioned at approximately a 60° angle relative to lateral fin 64.

Once the trial is positioned, a trial reduction is performed and the range of motion is checked. Adjustments to the insertion depth and rotational position of the prosthesis may be made as needed. Once the proper insertion depth and rotational orientation are achieved, the position of second clamp 50 relative to markings 32 on post 31 is noted. Screw 59 is then loosened and second clamp 50 is removed from post 31 and the trial prosthesis is removed from the intermedullary canal. Second clamp 50 is then removed from the trial prosthesis and secured to the middle suture hole 65 on anterior fin 62 of the prosthesis to be implanted. The prosthesis is then inserted into the intermedullary canal and opening 58 of second clamp 50 is engaged with post 31. The prosthesis is inserted until second clamp 50 reaches the predetermined location with respect to markings 32 on post 31. Second clamp 50 is then secured to post 31. The prosthesis is now in the predetermined position and may be cemented in place. The apparatus can also be used with prostheses approved for cementless fixation. The apparatus is removed after implantation.

In an alternative method, the humerus is prepared as described above. A trial that includes height indicia that indicate the insertion depth is then inserted into the intermedullary canal. Once the proper depth is reached the height indicators on the trial are noted. The trial prosthesis is then rotated to establish the proper retroversion. The humeral shaft is then notched adjacent the anterior fin to mark the proper retroversion. First clamp 20 is then positioned such that post 31 of depth gauge 30 is aligned with the notch. Clamp 20 is then secured to the shaft of the humerus. Second clamp 50 is then secured to the trial prosthesis and to post 31. Retroversion then may be checked by inserting guide 40 into opening 34 of base 33. If rod 40 is aligned with the forearm as described above, the prosthesis will be automatically at 30° of retroversion. Again, the retroversion can be adjusted as needed. A trial reduction is then performed and the range of motion checked. Once satisfaction orientation of the trial is achieved it is removed and the prosthesis is implanted. This may be done with or without the assistance of the positioning apparatus.

Although the present invention has been described in detail, the same is to be taken by way of example only and not by way of limitation. Numerous changes and modifications may be made to the embodiments disclosed without departing from the spirit and scope of the invention. For example, although use of the apparatus has been illustrated in connection with a shoulder prosthesis, the apparatus, or a slightly modified version, could be used with other prostheses, such as those used in total hip arthroplasty. Also, the predetermined retroversion angle can be changed by altering the relationship between the components. Accordingly, the present invention is to be limited only by the terms of the claims.

What is claimed is:

1. An apparatus for positioning a prosthesis in relation to either a first bone or a second bone, comprising:
    a body;
    a first clamp coupled to said body and operable to engage either said first bone or said second bone;
    a depth gauge coupled to said body; and
    a second clamp operable to engage said prosthesis, wherein (i) said second clamp is configured to be coupled to said depth gage at a first orientation for use with said first bone on a left side of a patient, and (ii) said second clamp is further configured to be coupled to said depth gage at a second orientation for use with said second bone on a right side of said patient.

2. The apparatus of claim 1, wherein:
    said second clamp includes (i) a first surface having a first indicia located thereon, and (ii) a second surface having a second indicia located thereon,
    said first surface is oriented proximally and said second surface is oriented distally when said second clamp is coupled to said depth gage at said first orientation, and
    said second surface is oriented proximally and said first surface is oriented distally when said second clamp is coupled to said depth gage at said second orientation.

3. The apparatus of claim 2, wherein:
    said first indicia includes at least the letter "R", and
    said second indicia includes at least the letter "L".

4. The apparatus of claim 1, wherein:
    said second clamp includes a clamp body,
    said clamp body has a passageway defined therethrough, and
    said depth gage extends through said passageway when said second clamp is coupled to said depth gage in at either said first orientation or said second orientation.

5. The apparatus of claim 4, wherein said clamp body further includes a fastener opening which intersects said passageway, further comprising:
    a fastener configured to advance through said fastener opening and into contact with said depth gage in order to couple said second clamp to said depth gage at either said first orientation or said second orientation.

6. The apparatus of claim 1, wherein said depth gage further includes depth positioning markings located thereon.

7. The apparatus of claim 1, wherein:
    said depth gage includes a post having a curved outer surface portion and a flat outer surface portion extending along the length of the depth gage, and
    said depth gage further includes depth positioning markings located on said flat outer surface.

8. The apparatus of claim 1, wherein:
    said second clamp includes a clamp body,
    said clamp body has a passageway defined therethrough,
    said depth gage extends through said passageway when said second clamp is coupled to said depth gage at either said first orientation or said second orientation, and
    said passageway is defined to be complementary in shape in relation to the shape of said depth gage.

9. An apparatus for positioning a prosthesis in relation to either a first bone or a second bone, comprising:
    a body;
    a first clamp coupled to said body and operable to engage either said first bone or said second bone;
    a post coupled to said body; and
    a second clamp operable to engage said prosthesis, wherein (i) said second clamp is configured to be coupled to said post at a first orientation for use with said first bone on a left side of a patient, and (ii) said second clamp is further configured to be coupled to said post at a second orientation for use with said second bone on a right side of said patient.

10. The apparatus of claim 9, wherein:
    said second clamp includes (i) a first surface having a first indicia located thereon, and (ii) a second surface having a second indicia located thereon,
    said first surface is oriented proximally and said second surface is oriented distally when said second clamp is coupled to said post at said first orientation, and said second surface is oriented proximally and said first surface is oriented distally when said second clamp is coupled to said post at said second orientation.

11. The apparatus of claim 10, wherein:

said first indicia includes at least the letter "R", and said second indicia includes at least the letter "L".

12. The apparatus of claim 9, wherein:

said second clamp includes a clamp body, said clamp body has a passageway defined therethrough, and said post extends through said passageway when said second clamp is coupled to said post in at either said first orientation or said second orientation.

13. The apparatus of claim 12, wherein said clamp body further includes a fastener opening which intersects said passageway, further comprising:

a fastener configured to advance through said fastener opening and into contact with said post in order to couple said second clamp to said post at either said first orientation or said second orientation.

14. The apparatus to claim 9, wherein said post futher includes depth position ing markings located thereon.

15. The apparatus according to claim 9, wherein:

said post includes a shaft having a curved outer surface portion and a flat outer surface portion extending along the length of the shaft, and said shaft further includes depth positioning markings located on said flat outer surface.

16. The apparatus according to claim 9, wherein:

said second clamp includes a clamp body, said clamp body has a passageway defined therethrough, coupled to said post at either said first orientation or said second orientation, and said passageway is defined to be complementary in shape relation to the shape of said post.

17. An apparatus for positioning a prosthesis, comprising:

a first mechanism operable to engage a body part of said patient;

a support member secured in relation to said first mechanism; and a second mechanism operable to engage said prosthesis, wherein (i) said second mechanism is configured to be coupled to said support member at a first orientation for use with a first bone on a left side of said patient, and (ii) said second mechanism is configured to be coupled to said support member at a second orientation for use with a second bone on a right side of said patient.

18. The apparatus of claim 17, wherein said first mechanism includes a clamp operable to engage said body part.

19. The apparatus of claim 18, wherein said body part includes a first bone or said a bone of said patient.

20. The apparatus of claim 17, wherein said second mechanism includes a clamp operable to engage said prosthesis.

21. The apparatus of claim 17, wherein:

said second mechanism includes (i) a first surface having a first indicia located thereon, and (ii) a second surface having a second indicia located thereon, said first surface is oriented proximally and said second surface is oriented distally when said second clamp is coupled to said support member at said first orientation, and said second surface is oriented proximally and said first surface is oriented distally when said second clamp is coupled to said support member at said second orientation.

22. The apparatus of claim 21, wherein:

said first indicia includes at least the letter "R", and said second indicia includes at least the letter "L".

23. The apparatus of claim 21, wherein said support member includes a depth gage for determining the depth of a stem of said prosthesis within an intramedullary canal of a bone of said patient.

\* \* \* \* \*